United States Patent [19]

Elseviers et al.

[11] Patent Number: 5,756,865
[45] Date of Patent: May 26, 1998

[54] METHOD FOR PRODUCTION OF TETRITOLS, SPECIFICALLY MESO-ERYTHRITOL

[75] Inventors: Myriam Elseviers, Kampenhout; Harald Wilhelm Walter Röper, Brussels; Roland Herwig Friedrich Beck, Everberg; Sonia Marianne Jeannine Coomans, Vilvoorde, all of Belgium

[73] Assignee: Cerestar Holding B.V., La Sas Van Gent, Netherlands

[21] Appl. No.: 724,784

[22] Filed: Oct. 3, 1996

[30] Foreign Application Priority Data

Oct. 4, 1995 [GB] United Kingdom ............... 9520231

[51] Int. Cl.$^6$ ............................ C07C 27/00; C07C 31/18
[52] U.S. Cl. ........................... 568/864; 568/861; 568/852
[58] Field of Search ............................ 568/861, 864, 568/852

[56] References Cited

U.S. PATENT DOCUMENTS 2,571,967  11/1951  Trenner .
3,478,112  11/1969  Adam .
5,426,246   6/1995  Nagahara .

FOREIGN PATENT DOCUMENTS 4444109  6/1996  Germany .

OTHER PUBLICATIONS

Journal of the American Chemical Society, vol. 71, No. 7, 21 Jul. 1949 Washington DC, US, pp. 2352–2355, N.R.Trenner et al"The Catalytic Reduction of the Esters of Tartaric Acid to the Erythritols".

Journal of the American Chemical Society, vol.70, No. 9, 30 Sep. 1948 Washington DC,US, pp. 3121–3125, H. Adkins, et al "The Hydrogenation of Esters to Alcohols at 25–150 Deg".

Journal of the American Chemical Society, vol.73,No.10, 5 Oct. 1951 Washington DC, US. pp. 4759–4761,R.K.Ness et al.: "The Reduction of Various Sugar Alcohols to Glycitols with Lithion Alumium Hydride".

Journal of the American Chemical Society, vol. 77, No. 14, 26 Jul. 1955 Washington DC, US, pp. 3766–3768, J.E. Carnahan, et al "Ruthenium–Catalysed Hydrogenation of Acids to Alcohols".

*Primary Examiner*—Gary Geist
*Assistant Examiner*—Karl Puttlitz
*Attorney, Agent, or Firm*—Cushman Darby & Cushman IP Group of Pillsbury Madison & Sutro, LLP

[57] ABSTRACT

The present invention discloses a chemical method for producing meso-erythritol. The method comprises catalytic hydrogenation of tartaric acid. The tetritol mixture resulting from the hydrogenation can be separated into its components. Alternatively selected components can be isomerized prior to such a separation.

24 Claims, No Drawings

METHOD FOR PRODUCTION OF TETRITOLS, SPECIFICALLY MESO-ERYTHRITOL

TECHNICAL FIELD

The present invention discloses a method for producing a tetritol. Specifically, the present invention relates to a method for producing meso-erythritol starting from tartaric acid. The method comprises a sequence of only one or two separate reaction steps. L-tartaric acid is hydrogenated to L-threitol and the product mixture is chemically isomerised to a tetritol mixture comprising meso-erythritol. The meso-erythritol may be further purified.

BACKGROUND OF THE INVENTION

It was recently found that meso-erythritol can be used as an alternative sweetener, erythritol has 60% of the sweetening power of sucrose, is highly crystalline, non-caloric and has the additional advantage of being non-cariogenic. The non-digestibility of meso-erythritol makes it ideally suitable for use in dietetic food applications. It has been suggested to use erythritol as a partial or total replacement for sucrose in chocolate, cakes, hard candy and ice-cream. The use of erythritol together with intense sweeteners has also been reported. Due to its favourable characteristics there is a growing interest in the application of this sugar alcohol Meso-erythritol can be produced by using erythritol-producing microorganisms. EP 0 136 802, EP 0 136 803, EP 0 136 804 and EP 0 136 805 describe an industrial-scale process for the production of erythritol by the aerobic fermentation of a sugar, e.g. glucose, or starch hydrolysate, with a sugar-tolerant yeast-like fungus *Moniliella tomentosa* var. pollinis or a substrain of the Moniliella organism. The conventional fermentation process has several drawbacks the most important being that the volume of the producing apparatus is large and that the production costs are rather high. Chemical synthesis of meso-erythritol may therefore be a viable alternative.

According to U.S. Pat. No. 2,796,444, a dialdehyde starch can be used to obtain meso-erythritol. When dialdehyde starch is subjected in solution or suspension in water to catalytic reduction in the presence of hydrogen gas and Raney-nickel as hydrogenation catalyst, several reactions occur simultaneously. Meso-erythritol is formed by hydrogenation of the aldehyde groups, hydrolysis of the polymer and subsequent hydrogenation of the newly formed aldehyde groups. This sequence of reactions results in the direct formation of meso-erythritol and ethylene glycol is formed as a by-product. The best results are obtained at temperatures of 180°–200° C., and hydrogen pressures of 12–14 MPa (120–140 bar). The main disadvantage of this direct hydrogenation is the low availablity of the starting material, the dialdehyde starch. Dialdehyde starch is prepared by the oxidation of starch with the expensive periodic acid or its salts. The electrochemical regeneration of periodate from iodate has been investigated to circumvent the high price of the periodate (U.S. Pat. No. 2,648,629), but dialdehyde starch still remains an expensive starting material and is not readily available.

According to U.S. Pat. No. 2,571,967, meso-erythritol is obtained in 60% yield by reducing a dialkyl ester of tartaric acid under closely controlled conditions. A solution of dialkyl ester of tartaric acid in a lower aliphatic alcohol is brought into contact with a suitable hydrogenation catalyst such as copper-chromite oxide and hydrogenated under high pressure of at least 20 MPa (200 bar) and at temperatures of about 125°–200° C. No reaction takes place below 14 MPa and large amounts of catalyst, preferably 50 to 100% by weight of the amount of ester used, are required. The main disadvantage of this reduction is the requirement of dialkyl esters of tartaric acid, comprising reactions in organic solvents and thus requiring explosion proof equipment, increasing to a large extend the investment costs. The use of copper-chromite oxide suffers from two drawbacks. Firstly, the catalyst is quickly coloured red after reaction, which proves to be the inactive type of the hydrogenation catalyst; this is an irreversible process. Secondly, the use of copper-chromite oxide requires high catalyst concentrations and extreme reaction conditions with respect to temperature and hydrogen pressure.

Other references describing the reduction of tartaric acid esters to the corresponding polyols are e.g. J. Am. Chem. Soc., 1948, 70, 3121, and J. Am. Chem. Soc., 1949, 71, 2352.

There exists a need for an economically feasible chemical method of producing tetritols, especially meso-erythritol, comprising a reaction sequence of a minimal number of reaction steps under mild reaction conditions, such as temperature, hydrogen pressure and low hydrogenation catalyst concentration. The starting material should preferably be a readily, abundantly available material.

SUMMARY OF THE INVENTION

The present invention provides such a method. The present invention relates to a method for the chemical production of meso-erythritol starting from a readily available acid, tartaric acid. L-tartaric acid is available in large amounts as a by-product of the wine-industry. The present invention discloses the direct reduction of tartaric acid to the corresponding polyol, using mild reaction conditions, with respect to temperature and hydrogen pressure.

The present invention relates to a chemical method for producing meso-erythritol from tartaric acid characterized in that the tartaric acid is submitted to catalytic hydrogenation.

The present invention further concerns a method which comprises the following steps:

a) catalytic hydrogenation of tartaric acid to a tetritol containing mixture, b) optionally catalytic isomerisation of the tetritol of step a), c) optionally separation of the desired tetritol from the product of step b).

By performing the catalytic hydrogenation a) in the presence of an acid, preferably phosphoric acid or boric acid, the L-threitol containing mixture directly contains a considerable amount of meso-erythritol. The meso-erythritol is then recoverable through chromatography as illustrated in Example 2 of the present description.

The present invention also concerns another method for obtaining an increased meso-erythritol yield. To achieve this increased yield the tartaric acid is first heated under alkaline conditions yielding meso-tartaric acid. Catalytic hydrogenation then results in an increased amount of meso-erythritol which can then be recovered by chromatographic methods. Alternatively, the mixture can be isomerised before separation. The method thus consists of the following steps:

a) treatment of L-tartaric acid with boiling alkali to obtain meso-tartaric acid, b) catalytic hydrogenation of meso-tartaric acid to meso-erythritol, c) optionally isomerisation of the product of step b).

The present invention can be summarised as follows. It discloses the catalytic hydrogenation under mild reaction conditions, with respect to temperature, hydrogen pressure and low hydrogenation catalyst concentration, of readily available L-tartaric acid, which results in $C_4$-polyols, followed by catalytic isomerisation. Starting with L-tartaric acid, L-threitol is obtained at first instance, which can be isomerised further to a tetritol mixture, containing predominantly meso-erythritol. Similarly D-tartaric acid, less abundantly available than L-tartaric acid, gives after catalytic hydrogenation D-threitol, which can be converted by chemical isomerisation to a tetritol mixture containing again predominantly meso-erythritol. Finally it is possible to use meso-tartaric acid as a starting material. Alternatively L-tartaric acid is isomerised in the presence of boiling alkali to a mixture containing meso-tartaric acid. The purified meso-tartaric acid gives after catalytic hydrogenation directly meso-erythritol. The present invention provides a method of producing polyols from acids characterized in that the acid is directly catalytically hydrogenated under mild reaction conditions, with respect to temperature, hydrogen pressure and using low hydrogenation catalyst concentration.

Ruthenium based hydrogenation catalysts proved to be particularly suitable for this process.

DETAILED DESCRIPTION OF THE INVENTION

The present invention relates to a chemical method for producing a tetritol from tartaric acid in which the tartaric acid is subjected to catalytic hydrogenation. The method is more particularly characterized as comprising the combination of steps of hydrogenating tartaric acid in the presence of a catalyst to yield a corresponding tetritol, optionally catalytically isomerizing the tetritol, and optionally separating the desired tetritol. According to the present method, tartaric acid is, in general, DL-tartaric acid, D-tartaric acid, meso-tartaric acid or L-tartaric acid. By preference, the tartaric acid is L-tartaric acid. The tartaric acid is hydrogenated under hydrogenation conditions. The hydrogenation is conducted in the presence of a suitable hydrogenation catalyst. The catalyst is preferably a ruthenium based hydrogenation catalyst.

The optional isomerization step can be performed in the presence of a hydrogenation/dehydrogenation catalyst which in turn can be promoted to the addition of alkali or acid. The optional isomerization step can, if desired, be performed simultaneously with the catalytic hydrogenation in the presence of an acid. By preference, the acid is phosphoric acid or boric acid.

According to the optional separation step, the tetritol produced can be obtained. By preference, the separation is performed using a cationic resin.

When L-tartaric acid is hydrogenated prior to isomerisation, the obtained tetritol is subjected to catalytic isomerisation by methods known in the art. The tartaric acid is hydrogenated at elevated temperatures, above 100° C., preferably at temperatures between 100° and 200° C., more preferably between 120° and 180° C. and even more preferably between 130° and 170° C. The elevated pressure of hydrogen gas is above 1 MPa, preferably at a pressure between 1 and 12 MPa and more preferably between 4 and 10 MPa in the presence of hydrogenation/dehydrogenation catalysts such as ruthenium, copper, palladium, platinum, rhodium, cobalt and nickel based catalysts, and in general metal oxides and mixtures thereof.

The polyol isomerisation can be performed at different pH levels, and the addition of alkali or acid has an influence on the thermodynamic equilibrium of the tetritol mixture. The isomerisation reaction results in a mixture comprising D,L-threitol and predominantly meso-erythritol. Meso-erythritol is present in these mixtures in more than 40% preferably in 50% or more. This reaction mixture further contains some other polyols, such as butanediols, butanetriol and glycerol, adding up to maximum 20%, preferably only to 10%.

The obtained polyol isomerisation mixture is optionally subjected to chromatography on cationic resin material yielding purified meso-erythritol with a purity in excess of 95%. Preferably the mixture is first demineralized and subsequent submitted to chromatography. The refining is suitably performed using a strong cation exchange resin e.g. Duolite C 26 followed by a medium base anion exchange resin Duolite A 368. This process is preferably repeated once. On plant scale chromatography is performed using suitable equipment obtainable for example from Mitsubishi with Diaion UBK-555 resin (in $Ca^{2+}$ form). The other tetritols are optionally recycled to the polyol isomerisation, resulting in increased overall yield. meso-Erythritol can also be purified by crystallisation.

The advantages of the process of the present invention in comparison with earlier described chemical processes such as those disclosed in U.S. Pat. No. 2,571,967 and U.S. Pat. No. 2,796,447 are manifold. The first is that readily available materials such as the abundantly available L-tartaric acid can be used for the catalytic hydrogenation. Furthermore, the reaction conditions such as temperature and hydrogen pressure are much milder and the catalyst concentration is much lower. The main advantage compared with other methods described in U.S. Pat. No. 2,796,447 is the requirement of less complicated unit operations, referring to the electrochemical regeneration of periodic acid, as is required to make the dialdehyde starch available.

Schematically the method of the present invention is illustrated in Scheme 1.

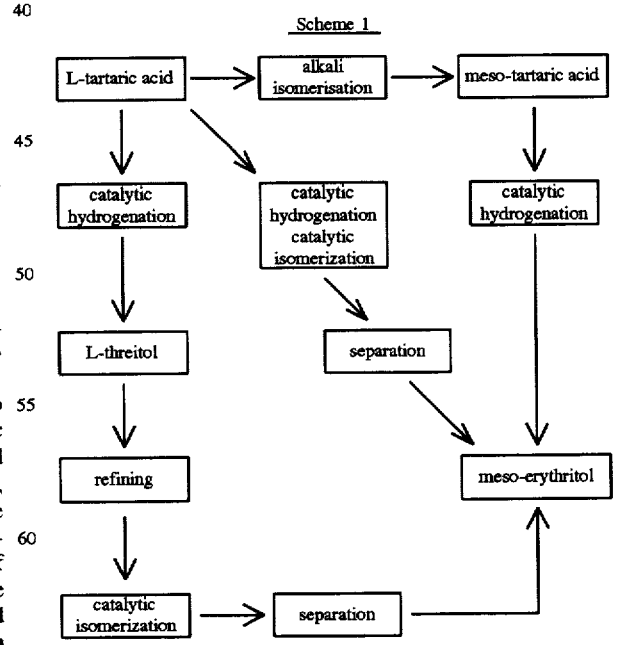

The invention is further illustrated by the following examples.

EXAMPLE 1

55 g L-tartaric acid was dissolved in 495 ml demineralized water. The mixture was hydrogenated on a Ruthenium catalyst (20% catalyst on total dry substance), which is supported on active carbon (5% Ru on carbon). The reaction temperature was 150° C. at a hydrogen pressure of 7 MPa. Within 6 hours no residual acid could be determined by HPLC using a cation exchange resin in $H^+$ form. The obtained hydrogenated mixture had the following composition:

| | |
|---|---|
| residual acid: | 0.7% |
| L-threitol: | 71.2% |
| erythritol: | 7.0% |
| glycerol: | 7.9% |
| 1,2,4-butanetriol: | 3.9% |
| 1,2,-butanediol: | 10.0% |

L-threitol and meso-Erythritol were separated from the other polyols in the hydrogenated mixture by chromatography on cation exchange resin in the calcium form.

Isomerisation of the tetritol mixture was performed at 150° C. and 4 MPa and 1% (based on total dry substance) phosphoric acid was added. After 6 hours the reaction was terminated. The obtained demineralized isomerisate had the following tetritol composition: meso-erythritol (41%), D,L-threitol (59%).

Meso-erythritol was separated by chromatography on cation exchange resin in the calcium form, yielding meso-erythritol with a purity of greater than 95%. D,L-threitol was recycled to the isomerisation.

The obtained meso-erythritol was crystallized.

EXAMPLE 2

55 g L-tartaric acid was dissolved in 495 ml demineralized water. The mixture was hydrogenated on a Ruthenium catalyst (20% catalyst on total dry substance), which is supported on active carbon (5% Ru on carbon). To the mixture phosphoric acid (2% on total dry substance) was added. The reaction temperature was 150° C. at a hydrogen pressure of 7 MPa. Within 6 hours no residual acid could be determined by HPLC using a cation exchange resin in $H^+$ form. The addition of phosphoric acid induces isomerisation during the hydrogenation. The obtained hydrogenated mixture had the following composition:

| | |
|---|---|
| residual acid: | 0.0% |
| L-threitol: | 57.6% |
| erythritol: | 14.5% |
| glycerol: | 10.8% |
| 1,2,4-butanetriol: | 4.1% |
| 1,2,-butanediol: | 13.0% |

L-threitol and meso-Erythritol were separated from the other polyols in the hydrogenated mixture by chromatography on cation exchange resin in the calcium form.

Meso-erythritol was crystallized from the tetritol mixture.

We claim:

1. A chemical method for producing a tetritol from tartaric acid which comprises the combination of steps of
   hydrogenating a tartaric acid in the presence of a catalyst to yield a corresponding tetritol; and simultaneously isomerizing the tetritol in the presence of an acid.

2. A chemical method according to claim 1, wherein the acid is phosphoric acid or boric acid.

3. A chemical method for producing a tetritol from tartaric acid which comprises the step of hydrogenating a tartaric acid using a ruthenium-based hydrogenation catalyst to yield the corresponding tetritol.

4. A chemical method according to claim 3, wherein said chemical method comprises the further steps of:
   catalytically isomerizing said tetritol, and
   optionally separating the tetritol from the product which was obtained by catalytically isomerizing said tetritol.

5. A chemical method according to claim 1, wherein the hydrogenating is performed in the presence of a ruthenium based catalyst.

6. A chemical method according to claim 1 or 3, wherein the hydrogenation is performed at a temperature between 100° C. and 200° C.

7. A chemical method according to claim 1 or 3, wherein the hydrogenation is performed at a temperature between 120° C. and 180° C.

8. A chemical method according to claim 1 or 3, wherein the hydrogenating is performed at a hydrogen pressure between 1–12 Mpa.

9. A chemical method according to claim 1 or 3, wherein the hydrogenating is performed at a hydrogen pressure between 4–10 Mpa.

10. A chemical method according to claim 1 or 3, wherein the tartaric acid is D,L-tartaric acid, meso-tartaric acid or L-tartaric acid.

11. A chemical method according to claim 8, wherein said tartaric acid is L-tartaric acid.

12. A chemical method according to claim 10, wherein said tartaric acid is L-tartaric acid.

13. A chemical method according to claim 4, wherein the isomerizing step is performed in the presence of a hydrogenation/dehydrogenation catalyst and a promoter comprising an alkali acid.

14. A chemical method according to claim 4, wherein the separation step is performed and wherein a cationic resin is used in said separation step.

15. A chemical method according to claim 3, wherein the hydrogenation is performed at a temperature between 100° C. and 200° C., a hydrogen pressure between 1 and 12 MPa in the presence of a ruthenium based catalyst, wherein said tartaric acid is D,L-tartaric acid, D-tartaric acid, meso tartaric acid or L-tartaric acid.

16. A chemical method according to claim 13, wherein the hydrogenating is performed at a temperature between 120°–180° C.

17. A chemical method according to claim 13, wherein the hydrogenating is performed at a hydrogen pressure between 4–10 MPa.

18. A chemical method according to claim 13, wherein the tartaric acid is L-tartaric acid.

19. A chemical method according to claim 1 or 3, wherein the hydrogenation is performed at a temperature between 120°–180° C. at a hydrogen pressure between 4–10 MPa and the tartaric acid is L-tartaric acid.

20. A chemical method according to claim 1 or 3, wherein meso-erythritol is produced.

21. A chemical method for producing meso-erythritol which comprises the combination of steps of:
   (a) conducting an isomerization of L-tartaric acid under alkaline conditions to yield meso-tartaric acid;
   (b) catalytically hydrogenating the thus obtained meso-tartaric acid to meso-erythritol; and
   (c) optionally isomerizing the meso-erythritol.

22. A chemical method according to claim 1, wherein said hydrogenating is conducted in the presence of an acid to obtain an L-threitol-containing reaction product, optionally refining the L-threitol-containing reaction product, catalytically isomerizing the L-threitol-containing product or the refined product, and separating the thus obtained meso-erythritol from the isomerization step.

23. A chemical method according to claim 13 wherein the hydrogenation/dehydrogenation catalyst is a ruthenium, copper, palladium, platinum, rhodium, cobalt or nickel-based catalyst.

24. A method according to claim 1 or 15, wherein the tartaric acid is in the form of an aqueous solution of said tartaric acid.

* * * * *